United States Patent [19]

Hengchang et al.

[11] Patent Number: 5,707,440
[45] Date of Patent: Jan. 13, 1998

[54] INORGANIC FILLER MATERIAL WITH RETENTION PROPERTIES, AND METHOD AND USE OF SUCH MATERIAL

[75] Inventors: Xu Hengchang, Beijing, China; Joachim Nagel, Friedrichsdorf, Germany

[73] Assignee: Heraeus Kulzer GmbH, Germany

[21] Appl. No.: 319,822

[22] Filed: Oct. 7, 1994

[30] Foreign Application Priority Data

Oct. 7, 1993 [DE] Germany .......................... 43 34 211.6

[51] Int. Cl.$^6$ .................................................. C04B 14/04
[52] U.S. Cl. ...................... 106/485; 106/35; 106/425; 106/426; 106/444; 106/482; 106/483; 106/484; 106/489; 428/403; 428/404; 428/406; 427/375; 427/376.1; 427/212; 501/17; 501/32
[58] Field of Search .................... 106/426, 425, 106/35, 444, 482, 483, 484, 485, 489; 428/403, 404, 406; 501/17, 32; 427/375, 376.1, 212

[56] References Cited

U.S. PATENT DOCUMENTS

| | | | |
|---|---|---|---|
| 3,066,112 | 11/1962 | Bowen | 523/116 |
| 3,505,785 | 4/1970 | Kirkland | 95/88 |
| 3,539,533 | 11/1970 | Lee, II et al. | 106/35 |
| 3,607,339 | 9/1971 | Davies | 106/468 |
| 3,656,921 | 4/1972 | Willcox | 106/446 |
| 3,864,443 | 2/1975 | Hopkins | 106/489 |
| 4,029,632 | 6/1977 | Gross et al. | 524/442 |
| 4,070,286 | 1/1978 | Iler et al. | 210/656 |
| 4,105,426 | 8/1978 | Iler et al. | 523/210 |
| 4,207,377 | 6/1980 | Kindrick | 106/426 |
| 4,215,033 | 7/1980 | Bowen | 523/115 |
| 4,306,913 | 12/1981 | Mabie et al. | 106/484 |
| 4,331,706 | 5/1982 | Kindrick | 106/425 |
| 4,336,301 | 6/1982 | Shaw | 428/323 |
| 4,381,918 | 5/1983 | Ehrnford | 106/35 |
| 4,392,828 | 7/1983 | Ehrnford | 106/35 |
| 4,491,482 | 1/1985 | Hori | 501/153 |
| 4,649,165 | 3/1987 | Kuhlmann | 523/116 |
| 5,346,546 | 9/1994 | Kaliski | 106/444 |

FOREIGN PATENT DOCUMENTS

| | | |
|---|---|---|
| 0 266 175 | 5/1988 | European Pat. Off. . |
| 0 271 236 | 6/1988 | European Pat. Off. . |
| 0 324 242 | 7/1989 | European Pat. Off. . |
| 0 345 581 | 12/1989 | European Pat. Off. . |
| 0 382 033 | 8/1990 | European Pat. Off. . |
| 2403211 C3 | 7/1975 | Germany . |
| 2405578 C3 | 8/1975 | Germany . |
| 27 11 014 | 9/1977 | Germany . |
| 26 41 548 | 12/1977 | Germany . |
| 3310838 A1 | 10/1983 | Germany . |
| 3403040 C2 | 8/1985 | Germany . |
| 41 05 319 | 8/1991 | Germany . |

OTHER PUBLICATIONS

Hawley's Condensed Chemical Dictionary, 11ed., Van Nostrand Rheinhold, NY, pp. 562,563, Dec. 1987.
Ullmann's Encyclopedia of Industrial Chemistry, vol. A8, 1987, pp. 281–283, no month.
Patent Abstracts of Japan, C–636, (1989), vol. 13, No. 417 of JP–OS 1–156370, no month.
Patent Abstracts of Japan C–564, (1989, vol. 13, No. 42, of JP–OS 63–240937, no month.
Derwent Abstracts 85–185882, no date.

Primary Examiner—Mark L. Bell
Assistant Examiner—Scott L. Hertzog
Attorney, Agent, or Firm—Frishauf, Holtz, Goodman, Langer & Chick, P.C.

[57] ABSTRACT

A finely divided inorganic filler material is a sintered composite which consists of larger macro-filler particles of glass and of smaller micro-filler particles of glass or ceramics partially covering the macro-filler particle and firmly connected to it by sintering. Plastic materials reinforced with the filler are distinguished by improved abrasion resistance.

14 Claims, 1 Drawing Sheet

INORGANIC FILLER MATERIAL WITH RETENTION PROPERTIES, AND METHOD AND USE OF SUCH MATERIAL

FIELD OF THE INVENTION

The invention relates to a finely divided inorganic filler, a method for producing it and its use in plastic materials. The filler material is preferably used in dental materials and coating materials on a plastic base.

BACKGROUND

In the field of tooth filling materials which are cured by polymerization it was considered to be a great step forward when Rafael L. Bowen introduced long-chain monomeric dimethacrylate reaction products of bisphenol A and its derivatives with glycidyl methacrylate, in particular the so-called bis-GMA; and fine quartz glass powder for reinforcement of the plastic matrix in place of the methyl methacrylate used up to then (U.S. Pat. No. 3,066,112).

A further example of a dental material containing, in addition to organic monomers, a finely divided inorganic filler is described in U.S. Pat. No. 3,539,533. The polymerizable binder in this case is a mixture of bis-GMA, bisphenol A-dimethacrylate, diluted monomers, in particular triethylene glycol dimethacrylate and, if required, methacrylic acid in small amounts which is used, together with approximately 65 to 75 weight-% of the inorganic filler, for example silicon dioxide, glass, aluminum oxide or quartz. The inorganic filler can be of a particle size of approximately 2 to 85 micrometers; for improving the bond between filler and resin/filler is pretreated with silane, for example 3-methacryloyl oxypropyl trimethoxysilane.

Fillings for teeth, caps, artificial teeth and the like, having good mechanical properties, can be produced from dental materials (composites) containing inorganic fillers of the most varied chemical composition—mainly of glass, ceramic materials or glass-ceramic materials which have been treated with silane materials to improve the adhesion between filler and resin.

The use of micro-fine inorganic fillers with average particle sizes between 0.01 to 0.4 micrometers also resulted in dental plastic products which were improved in the esthetic sense. These products could be polished to a high gloss and have a transparency similar to that of natural teeth (DE 24 03 211 C3).

The so-called hybrid materials represent a further step in the development of resin based dental materials which contain micro-fine fillers as well as conventional fillers (macro fillers). Such a dental material is known, for example, from DE 24 05 578 C3. It contains 30 to 80 weight-% of a mixture of amorphous silicic acid produced by means of flame hydrolysis (pyrogenous silicon dioxide) of a maximum particle size of 0.07 micrometers and finely divided glass, preferably boron silicate glass, glass containing barium oxide or lanthanum oxide or lithium aluminum silicate glass of a particle size of up to 5 micrometers.

The dental filler described in DE 34 03 040 C2 contains 60 to 90 weight-% of a filler mixture of 5 to 20 weight-% of a filler opaque to X-rays with a particle size distribution between 0.5 and 40 micrometers, 20 to 35 weight-% of a filler opaque to X-rays with a particle size distribution between 0.2 and 15 micrometers and 45 to 75 weight-% of a silicon dioxide micro-filler with a particle size distribution between 5 and 150 nanometers.

A further example of a hybrid material is the dental material described in EP 382 033 A2 which contains, in addition to polymerizable acrylates or methacrylates and a catalyst for photo-polymerization (photo activator), 5 to 80 weight-% of silanized glass or silanized glass-ceramics with a mean particle size between 0.1 and 10 micrometers and 2 to 10 weight-% of a surface-treated micro-filler. The inorganic fillers used for reinforcing resin based dental materials mostly have a surface treated with a silane, for example 3-methacryloyl oxypropyl trimethoxy silane, which improves the compatibility with the organic components (DE 34 03 040 C2) and causes a chemical adhesion between the filler and the plastic matrix. A further improvement of the filler/plastic bond can be achieved when the possibility of a physical adhesion exists in addition to the chemical adhesion. In accordance with a proposal in U.S. Pat. No. 4,215,033, for example, physical adhesion can be provided by the use of a semi-porous filler obtained by etching a two-phase glass.

If abrasive forces act on products made of plastics which have been reinforced with finely divided inorganic fillers, the surface of the softer plastic matrix is worn down without damaging the filler particles themselves. With continuing abrasion of the plastic matrix, sufficient matrix is removed so that the filler particles on the surface lose their hold on the plastic matrix and break away (as illustrated in FIGS. 2a–e). For example, with composite dental materials, the deterioration caused by abrasion during chewing and tooth brushing can be great enough so that the fillings have to be prematurely renewed.

SUMMARY OF THE INVENTION

It is therefore an object of the invention to provide a finely divided inorganic filler for plastics which is retained in the surface of the plastic matrix even after extended abrasive action has occurred to wear away the surface of the plastic matrix filled with the inorganic filler particles. The filler particles should be easy to silanize—in the sense of even silanization—and should be well wetted by the plastic matrix or the monomers forming it.

It is a further object to provide a method for producing an inorganic filler which is intended for use in polymerizable dental materials and for reinforcing plastic materials.

The finely divided filler by means of which the invention objects can be attained is distinguished in accordance with the invention in that it is a composite filler made of macro-filler particles and micro-filler particles. Each composite filler particle consists of a macro-filler particle of glass, and a number of micro-filler particles of glass or ceramics partially covering the macro-filler particle and being firmly connected with it by sintering.

The composite filler has especially proven itself if it has a mean particle size between 0.3 to 12.0 micrometers, the macro-filler particle has a mean particle size between 0.2 and 10.0 micrometers, particularly 0.2 to 2.0 micrometers, and the micro-filler particle has a mean particle size between 0.01 and 1.5 micrometers, preferably 0.01 to 0.3 micrometers.

The weight ratio of macro-filler to micro-filler particles in the composite filler preferably lies at 1:1–12; the ratio of the diameters of the macro-filler particles to the micro-filler particles is 5–20:1.

The surface of the composite filler particles in accordance with the invention is distinguished by a micro-structure with good retention properties, formed by micro-filler particles which are characteristically arranged on the macro-filler particles. The composite filler particles can be evenly silanized and can be well wetted with monomers during mixing.

Because of the micro-structure with good retention properties, the particles of the composite filler remain anchored in the plastic matrix even if they project out of the matrix by two-thirds of their volume.

The statements made in regard to the micro-structure of the composite filler particles and their anchoring in the matrix are illustrated by the drawings containing FIGS. 1, 2 and 3.

DETAILED DESCRIPTION

Figure 1:
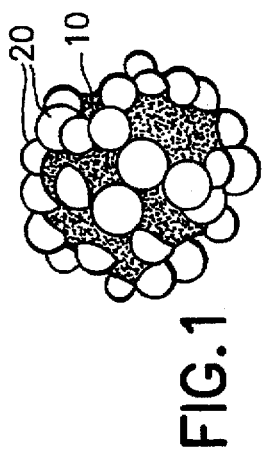
FIG. 1 is a schematic representation of composite filler particles made of macro-filler particles 10 forming the core and micro-filler particles 20 bonded to it.
Figure 2A:
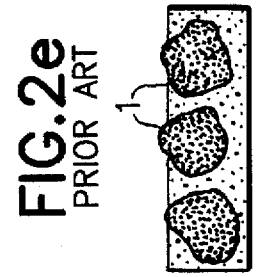
FIGS. 2a to 2e represent in a schematic view the behavior of particles of a known filler 1 during abrasive wearing away of the plastic matrix 3.
Figure 2B:
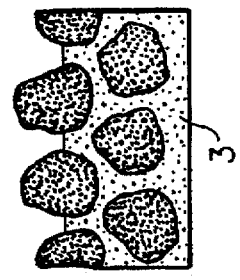
Figure 2C:
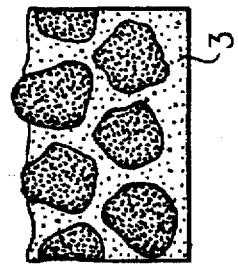
Figure 2D:
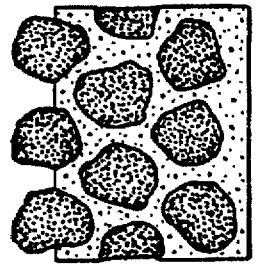
Figure 2E:
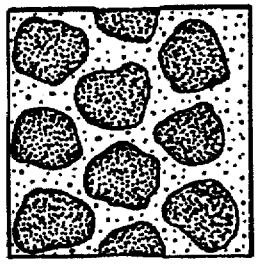
Figure 3A:
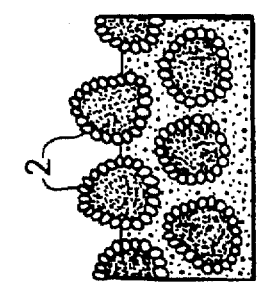
FIGS. 3a to 3e represent particles of the composite filler 2 of the invention in the plastic matrix 3 during abrasive wearing away of the plastic matrix 3.
Figure 3B:
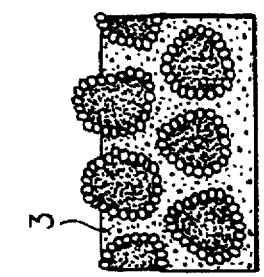
Figure 3C:
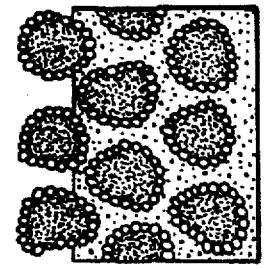
Figure 3D:
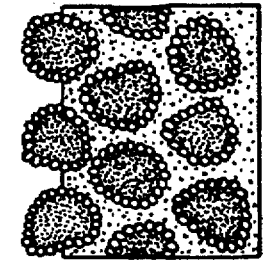
Figure 3E:
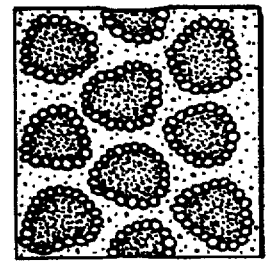

The materials constituting the composite filler of the invention must be insoluble and—if the composite filler is intended for dental purposes—bio-compatible. The macro-filler particles preferably consist of boron silicate glass or aluminum silicate glass, such as glass made of barium borosilicate or lithium aluminosilicate and barium aluminosilicate. The micro-filler particles also consist of glass or a ceramic material. Suitable ceramic materials are the nitride, carbide or oxide of one of the elements silicon, zirconium, aluminum or titanium. $SiO_2$, $ZrO_2$, $Al_2O_3$ and $TiO_2$ have particularly proven themselves.

In a preferred embodiment the macro-filler particles have a lower melting point than the micro-filler particles. It has been proven to be particularly advantageous to select the macro-filler particles and the micro-filler particles in such a way that their melting points differ by at least 40° C. especially to facilitate this sintering together of the particles as described below.

A further embodiment of the invention is a method for producing the composite fillers of the invention which is distinguished in that an intimate mixture of macro-filler particles and micro-filler particles is produced, the mixture is sintered if required, and thereafter the sintered product is ground dispersed in a liquid using an ultrasonic treatments. Coarser particles possibly contained in the dispersion settle during standing whereafter the dispersed particles are recovered from the liquid As noted above, the macro-filler particles should have a lower melting point than the micro-filler particles.

The method is preferably executed with macro-filler particles and micro-filler particles, the melting points of which differ by at least 40° C. The macro-filler particles preferably having the lower melting point.

It was proven to be particularly effective to employ macro-filler particles of a mean particle size between 0.2 and 10.0 micrometers, preferably 0.2 to 2.0 micrometers, and micro-filler particles of a mean particle size between 0.01 and 1.5 micrometers, preferably 0.01 to 0.3 micrometers, and to use the macro-filler and micro-filler particles at a weight ratio of 1:1–12.

Regarding their size, the macro-filler particles and the micro-filler particles are selected such that the ratio of their diameters is 5–20:1.

The sinter temperature depends on the type of the macro-filler and micro-filler particles and generally is between 650° to 1200° C. The temperature is selected such that during sintering the macro-filler melts or starts to melt and the micro-filler remains in the solid state.

The individual steps of the method of the invention will be more particularly described in the following:

Mixing

Macro-filler particles of a mean particle size between 0.2 and 10.0 micrometers are intimately mixed with micro-filler particles of a mean particle size between 0.01 and 1.5 micrometer at a weight ratio of 1:1–12 in a ball mill or other mixer suitable for mixing solids, while adding a liquid, such as water/ethanol. The exact weight ratio of the macro-filler to the micro-filler depends on the melting point, the particle size and the particle size distribution of the fillers and can be determined by prior tests. Mixing time is a function of the grinding speed of the ball mill of other mixer suitable for mixing solids and the amount of filler.

Sintering

After removal of the liquid contained in it, the intimate mixture is sintered for approximately 1 to 3 hours at approximately 650° to 1200° C. The exact sintering conditions depend on the properties and amounts of the fillers and can be determined by prior tests.

Optional Grinding

If required, the sintered product can be ground prior to the dispersion step.

Dispersion

The sintered product is evenly suspended in a liquid, for example water/ethanol, using ultrasonic waves.

Separation

Coarser particles possibly contained in the suspension settle in the suspension during standing. The particle-like composite filler is separated from the suspension (from which the coarser particles were removed) by centrifuging, and is thereafter dried.

Yield is 40 to 70%; the mean particle size of the composite filler lies between 0.3 and 12.0 micrometers.

Silanizing

The composite filler can be silanized prior to or following centrifuging in a manner known per se by treatment with a silane, for example 3-methacryloyl oxypropyl trimethoxy silane.

To explain the invention in detail, the production of a finely divided composite filler in accordance with the invention and a formulation containing the composite filler for use as a dental material which can be polymerized by irradiation with light will be described in the examples which follow. The abrasion resistance of the cured dental material will be determined and compared with commercially available dental materials after curing.

EXAMPLE 1

Production of the Composite Filler 10 g of barium aluminum silicate glass of a mean particle size of 0.7 micrometers and 150 g micro-fine silicon dioxide of a mean particle size of 0.04 micrometers (Aerosil OX50 (commercially available from Degussa, Germany)) are intimately mixed in the presence of 1500 ml of a water/ethanol mixture (85:15) for 80 hours in a ball mill. Subsequently the mixture is dried in air at 105° C. and sintered at approximately 850° for three hours. After cooling to room temperature and addition of ten times the amount of a water/ethanol mixture (85:15), the sintered product is mixed with 100 ml of a 15% solution of 3-methacryloyl oxypropyl trimethoxy silane in ethanol and the mixture obtained in this way is subjected to ultrasonic waves for eight hours whereby the sintered product in the mixture is dispersed and silanized. Following this, the mixture is allowed to stand for three hours so that coarser particles can settle, the coarser particles are removed. The resulting mixture is separated into solid and liquid by centrifuging at 2800 rpm. After drying of the solid in air at 105° C., 110 g of the desired composite filler of a mean particle size of 0.5 to 3 micrometers are obtained.

EXAMPLE 2

Production of the Composite Dental Material 100 g of a polymerizable resin as a binder are obtained by mixing 54.24 g of bis-GMA, 44.33 g of triethylene glycol dimethacrylate 0.99 g of 2-(2-hydroxy-5-methylphenyl)-benzotriazol 0.16 g of camphor quinone, and 0.28 g of 2-diethyl aminoethyl methacrylate.

A tooth filling material in the form of a homogeneous paste which is particularly suitable for the occlusal area of the teeth is made by mixing 30 g of the polymerizable resin as a binder, 68 g of the finely divided composite filler described in Example 1 and 2 g of a micro-fine silicon dioxide of a mean particle size of 0.04 micrometers (Aerosil OX50—Degussa, Germany).

Samples of the tooth filling material are placed into small glass tubes (interior diameter 10 mm, height 6 mm) and irradiated for 360 seconds with a light device. The determination of the abrasion resistance of the test bodies obtained in this way is provided by way of measuring the loss in volume as described in the Journal of Oral Rehabilitation, 1990, vol. 17, 107–115. For comparison, polymeric test bodies made in a corresponding way from four commercially available tooth filling materials of the composite type are tested. The volume loss of the test bodies measured after 2000 cycles in the form of a mean value of ten measurements, the standard deviation and the variance (standard deviation/mean value) are shown in the table, which follows:

What is claimed is:

1. A method for producing a finely divided inorganic filler comprising composite filler particles made of macro-filler particles and micro-filler particles; and wherein the composite filler particle has a mean particle size between 0.3 and 12 micrometers; comprising the steps of providing macro-filler particles and micro-filler particles wherein the macro-filler particles are larger than the micro-filler particles and have a lower melting point, the macro-filler particles consist of glass and have a mean particle size between 0.2 and 10 micrometers, and the micro-filler particles consist of a nitride, carbide or oxide of one of the elements silicon, zirconium or aluminum and have a mean particle size between 0.01 and 1.5 micrometers;

mixing the macro-filler particles and the micro-filler particles to produce an intimate mixture thereof;

sintering the mixture to secure the micro-filler particles to the surface of the macro-filler particles to form a sintered product;

dispersing the sintered product in a liquid using ultrasonic waves;

allowing coarser sintered product particles to settle from the dispersion; and centrifuging the dispersion to recover the finely divided inorganic filler.

2. The method in accordance with claim 1, wherein the macro-filler particles have a melting point at least 40° C. lower than the micro-filler particles and the sintering step comprises heating the mixture to melt the surface of the macro-filler particles.

3. The method in accordance with claim 1, wherein the mixture of macro-filler particles and micro-filler particles is sintered in the range of 650° to 1200° C.

4. The method in accordance with claim 1, wherein the macro-filler particles are made of borosilicate glass or aluminosilicate glass.

5. The method in accordance with claim 1, wherein the micro-filler particles consist of $SiO_2$, $ZrO_2$ or $Al_2O_3$.

6. The method in accordance with claim 1, further comprising treating the composite filler with a silane.

7. The method in accordance with claim 6, wherein the silane is 3-methacryloyl oxypropyl trimethoxy silane.

TABLE

| Example | Product | Trade name | Loss of volume | | |
|---|---|---|---|---|---|
| | | | Mean [mm$^3$] | Standard Deviation | Variance [%] |
| 2 | Dental material with composite filler particles | | 43.8 | +/−1.31 | 2.98 |
| 3 (Comparison) | Dental material with fine particle hybrid | Z 100 (1) | 50.81 | +/−0.88 | 1.72 |
| 4 (Comparison) | Dental material with fine particle quartz hybrid | Pertac hybrid (2) | 69.3 | +/−7.10 | 10.20 |
| 5 (Comparison) | Dental material with coarse particle hybrid | Estilux hybrid VS (3) | 93.65 | +/−13.59 | 14.51 |
| 6 (Comparison) | Dental material hybrid for posterior | P-50 (1) | 100.5 | +/−6.91 | 6.88 |

(1) Minnesota Mining & Manufacturing Co., USA
(2) Espe Fabrik pharmazeutischer Präparate, Germany
(3) Heraeus Kulzer GmbH, Germany Various changes and modifications may be made, and features described in connection with any one of the embodiments may be used with any of the others, within the scope of the inventive concept.

8. The method in accordance with claim 1, wherein the macro-filler particles and the micro-filler particles are present in a weight ratio of 1:1–12.

9. The method in accordance with claim 8, wherein the macro-filler particles have a mean particle size between 0.2 and 2 micrometers and a melting point at least 40° C. lower than the micro-filler particles; and the sintering step comprises heating the mixture to soften or melt the surface of the macro-filler particles.

10. The method in accordance with claim 9, wherein the mixture of macro-filler particles and micro-filler particles is sintered in the range of 650° to 1200° C.;

the macro-filler particles are made of borosilicate glass or aluminosilicate glass; and the micro-filler particles are made of $SiO_2$, $ZrO_2$ or $Al_2O_3$.

11. The method in accordance with claim 10, further comprising treating the composite filler with a silane, and wherein the silane is 3-methacryloyl oxypropyl trimethoxy silane.

12. The method in accordance with claim 1, wherein the macro-filler particles and the micro-filler particles are present in a weight ratio of 1:1–12;

the macro-filler particles have a melting point at least 40° C. lower than the micro-filler particles and the sintering step comprises heating the mixture to soften or melt the surface of the macro-filler particles;

the macro-filler particles are made of borosilicate glass or aluminosilicate glass; and the micro-filler particles are made of $SiO_2$, $ZrO_2$ or $Al_2O_3$.

13. The method in accordance with claim 1 further comprising that the sintered product is ground prior to ultrasonic treatment.

14. The method of claim 1 wherein the macro-filler particles have a mean particle size between 0.2 and 2 micrometers and the micro-filler particles have a mean particle size between 0.01 and 0.3 micrometers.

* * * * *